United States Patent [19]

Theodoropulos

[11] Patent Number: 4,714,763
[45] Date of Patent: Dec. 22, 1987

[54] NOVEL OXAZINE-UREAS AND THIAZINE UREA CHROMOPHORS AS FLUORESCENT LABELS

[75] Inventor: Spyros Theodoropulos, Yorktown Heights, N.Y.

[73] Assignee: Viomedics Inc., Worcester, Mass.

[21] Appl. No.: 753,937

[22] Filed: Jul. 11, 1985

[51] Int. Cl.$^4$ .................. C07D 265/38; C07D 279/36
[52] U.S. Cl. ........................................ 544/31; 544/37; 544/101; 544/103
[58] Field of Search ...................... 544/31.37, 101, 103

[56] References Cited

U.S. PATENT DOCUMENTS

| 3,894,012 | 7/1975 | Baumann et al. ................. 544/103 |
| 4,018,763 | 4/1977 | Moser et al. |
| 4,622,395 | 11/1986 | Bellus et al. ..................... 544/37 |

Primary Examiner—Richard L. Raymond
Attorney, Agent, or Firm—William R. Moran

[57] ABSTRACT

Novel urea derivatives of oxazine and thiazine chromophors have the structural formula I or II.

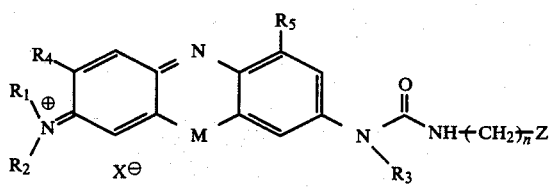

I

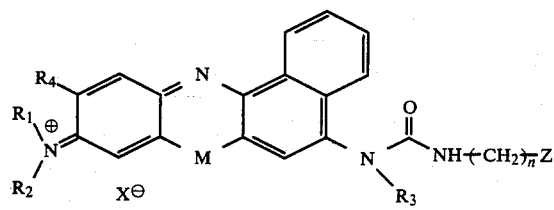

II wherein M is oxygen or sulfur, $R_1$ and $R_2$ are aliphatic alkyl groups or hydrogen; $R_3$ is hydrogen or alkyl group; $R_4$ is hydrogen, alkyl or amine group; $R_5$ is hydrogen, amine or alkyl group; $X^\ominus$ is an anion consisting of an organic (e.g. $CH_3COO^\ominus$, $CH_3CH_2COO^\ominus$ and the like) or inorganic specie (e.g. $Cl^\ominus$, $Br^\ominus$, $I^\ominus$, $ClO_4^\ominus$, $SO_4''$, and the like); n is 0 to 20; Z is $N{=}C{=}O$, $N{=}C{=}S$, carboxylic, primary or secondary amine, and when n=0, Z may be

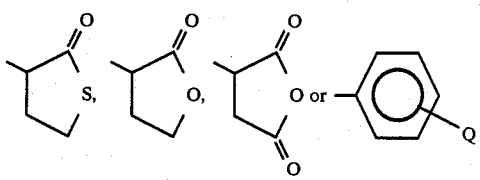

wherein Q is hydroxyl, amino, carboxylic, sulfydryl, isocyanato, or isothiocyanato.

The functional oxazine-urea and thiazine-urea derivatives react with compounds of interest to form adducts resulting in the fluorescent labeling of the compound.

8 Claims, No Drawings

NOVEL OXAZINE-UREAS AND THIAZINE UREA CHROMOPHORS AS FLUORESCENT LABELS

FIELD OF THE INVENTION

This invention relates to novel urea derivative of oxazine type chromophors such as, for example, Nile blue A and to thioazine type chromophors such as, for example, toluidine blue O useful in the fluorescent labeling of organic substrates. The urea derivatives of the invention have the ability to react with compounds of biological or clinical interest to form adducts resulting in the fluorescent labeling of the compounds.

The novel compounds are intended for use in analytical techniques for the detection and measurement of biological and clinical compounds of interest. Typical examples of such compounds are bacteria, viruses, enzymes, blood groups and hormones (drugs).

DESCRIPTION OF THE PRIOR ART

It is known that fluorescent groups such as fluorescein isothiocyanate can be introduced into biological or clinical compounds of interest. Analytical techniques employing fluorescein frequently lack the requisite sensitivity for the detection and measurement of nanomolar or picomolar levels of organic substrates. The lack in sensitivity of techniques which employ fluorescein is believed to be due to a high degree of overlap in fluorescent excitation and emission spectra and to high background fluorescence exhibited by biological fluids. Furthermore, the applicability of fluorescein is limited since it only attaches to compounds having displacable amine moieties such as proteins, peptides or amino acids.

Accordingly, it is an object of the present invention to provide novel urea derivatives of oxazine type chromophors which may be readily coupled to compounds of clinical or biological interest to provide derivatives which exhibit intense fluorescence. A further object of the invention provides for fluorescent labeling of biological molecules which circumvent the limitations of background fluorescence implicated in immunological assays. Yet another object of this invention lies in the coupling of the novel moieties to form adducts with a broad spectra of biological and clinical compounds by facile and gentle chemical reactions. Other objects and advantages of the present invention will become apparent from the following detailed description of the present invention.

While the invention is susceptible to various modifications and alternative forms, there will herein be described in detail the preferred embodiments. It is not intended to limit the invention to the specific forms disclosed. On the contrary, it is intended to cover all modifications and alternative forms falling within the spirit and scope of the invention as expressed in the appended claims.

SUMMARY OF THE INVENTION

The present invention is directed to novel urea derivatives of oxazine type chromophors which contain moieties which allow the coupling of these chromophors to a variety of biological molecules of clinical interest. The resulting derivatives provide intense fluorescent haptens, antigens, drugs and antibodies which can be used in the development of fluorescent analytical techniques. A number of oxazine type chromophors such as Cresyl violet, Brilliant cresyl blue, Nile blue A, oxazine, etc., have been derivatized through a urea linkage to functional derivatives without effectively changing the fluorescent characteristics (e.g. excitation, emission) of the subject chromophors. The basic structures of the uread-oxazines are structurally represented by the structural formulas I and II.

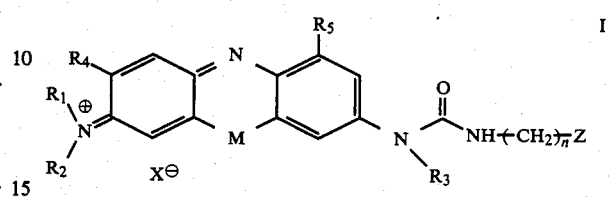

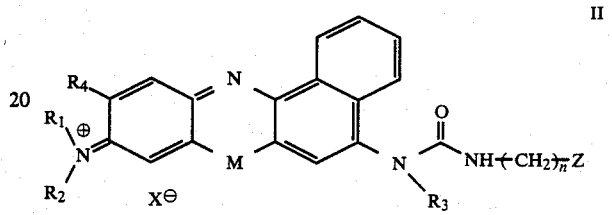

wherein M is O or S; $R_1$ and $R_2$ are aliphatic alkyl groups or hydrogen; $R_3$ is hydrogen or aliphatic alkyl group; $R_4$ is hydrogen, alkyl or amino; $R_5$ is hydrogen, amino or alkyl group; $X^-$ is an anion consisting of an organic or inorganic specie such as, for example, $Cl^-$, $Br^-$, $I^-$, $ClO_4^-$, $SO_4^{-2}$, $CH_3COO^-$, $CH_3CH_2COO^-$; n is 0–20; Z is $N{=}C{=}O$, $N{=}C{=}S$, carboxylic, primary or secondary amino, and when n=0, Z may be

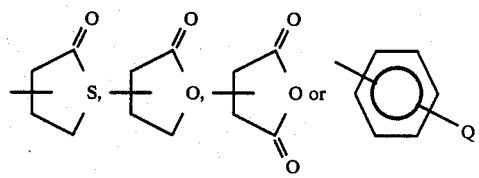

wherein Q is hydroxyl, amino, carboxylic, sulfydryl, isocyanato or the structural formula II.

Typical examples of oxazine and thiazine chromophors are shown below, both by structural formula and name.

Nile blue A

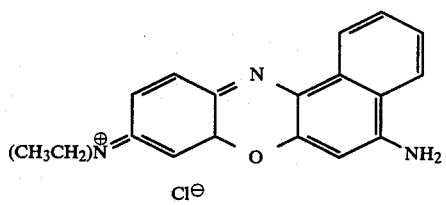

Toluidine blue O

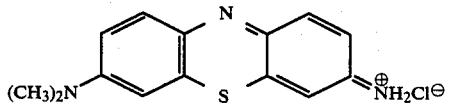

DETAILED DESCRIPTION OF THE INVENTION

The oxazinyl urea compounds of the invention are bi-functional. The oxazinyl urea moiety represented structurally as I and II

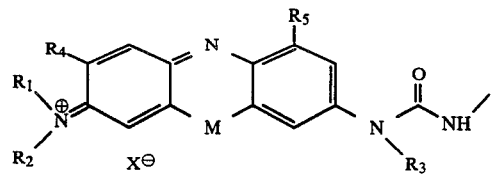

or

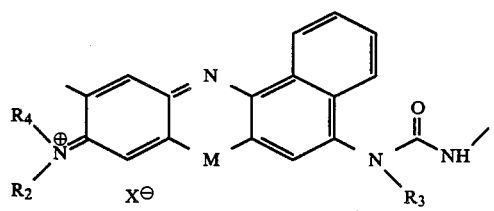

act as an ideal fluorescent agent due to its attractive fluorescence emission exhibited at wavelengths above 580 nanometers. The remaining moiety of the invention compounds, represented by the radical $-(CH_2)_n-Z$,

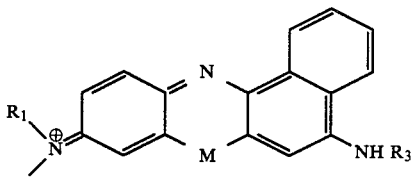

with a bi-functional isocyanate of the general formula:

$$O=C=N-(CH_2)_n-Z$$

wherein when n is 0, Z is lactone, thiolactone or succinic anhydride, and when n is 1 to 20, Z is isothiocyanate, isocyanate, blocked carboxylic or benzene derivatives such as

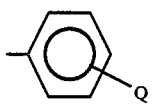

where Q is blocked primary or secondary amine, blocked carboxylic, isocyanate or isothiocyanate was preferred.

An example demonstrating the derivatization of Nile blue A is illustrated in the following equation:

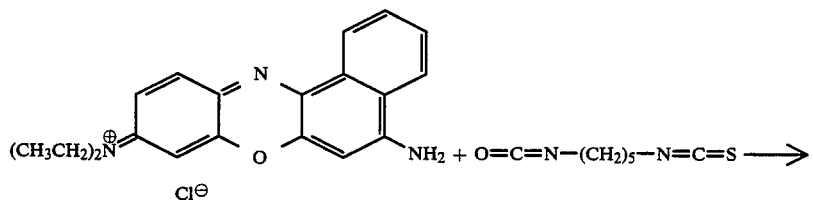

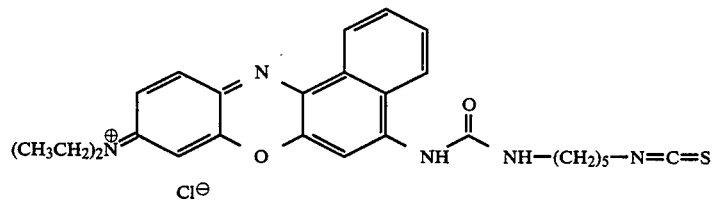

where Z is an isocyanate, isothiocyanate, lactone or thiolactone moiety, provides an active hydrogen bonding site and functions most suitably to promote coupling of the oxazinyl urea with organic substrates of interest. The oxazinyl and thiazinyl ureas of the invention were synthesized using known techniques. For example, the reaction of the oxazine and thiazine chromophors of the general formulas Ia or IIa

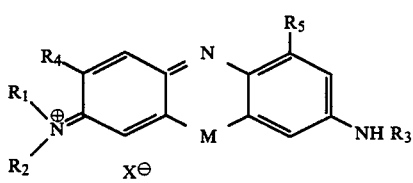

The synthesis was optionally performed in the presence of a solvent which was inert to the reaction partners such as aromatic hydrocarbons, e.g. benzene, toluene, xylene or aliphatic or aromatic chlorinated hydrocarbons as esters, ketones or amides with pyridine being the preferred solvent. The temperature employed in the synthesis may range from 5° to 150° C. with ambient temperature being preferable.

The oxazinyl ureas of the invention may be reacted with any compound of interest capable, of course, of reacting with the Z radical. For example, any compound containing (in the classical sense) an active hydrogen group may be coupled to the oxazinyl ureas, e.g. any compound containing a hydroxyl, amino, sulfhydryl or carboxylic group can be utilized. Accordingly, a wide number of amino acids, peptides, proteins, enzymes, steroids, drugs, pesticides, various natural products, plant and animal hormones, polyamines, viruses, bacterial cells and other metabolites contain groups reactive with the Z radicals.

The oxazinylurea chromophors can be bound to organic substrates through the Z moiety to form adducts by utilizing known process conditions. It is suitable to prepare the adduct by reaction in a solvent, if desired, at a temperature ranging from ambient to about 150° C. Representative examples of useful solvents include pyridine, dimethylformamide, tetrahydrofuran, triethylamine, ethers, methylene chloride and the like, with pyridine being preferred. Also, if desired, any of the several types of catalysts known to be useful in forming urethanes, ureas, thioureas and amides can be employed.

Useful catalysts include tertiary amines, salts or organic acids with a variety of metals such as alkali metals and the like.

The oxazino urea chromophors of the invention were coupled to biological or clinical compounds of interest through the Z moiety in various ways to form adducts.

For example, when the Z moiety is isocyanate, as in isocyanatohexyl-Nile blue O urea, the chormophor is well-suited to coupling with an organic substrate containing a functional group having an active hydrogen group selected from the group consisting of hydroxyl, amino, sulfhydryl and carboxylic. Typical organic substrates are digoxin, cortisol, estradiol and, in general, drugs or hormones having reactive hydroxyl groups. For example, cortisol can be coupled to isocyanatohexyl-ureado-Nile blue O in accordance with the invention by a carbamate bond as shown in the following equation:

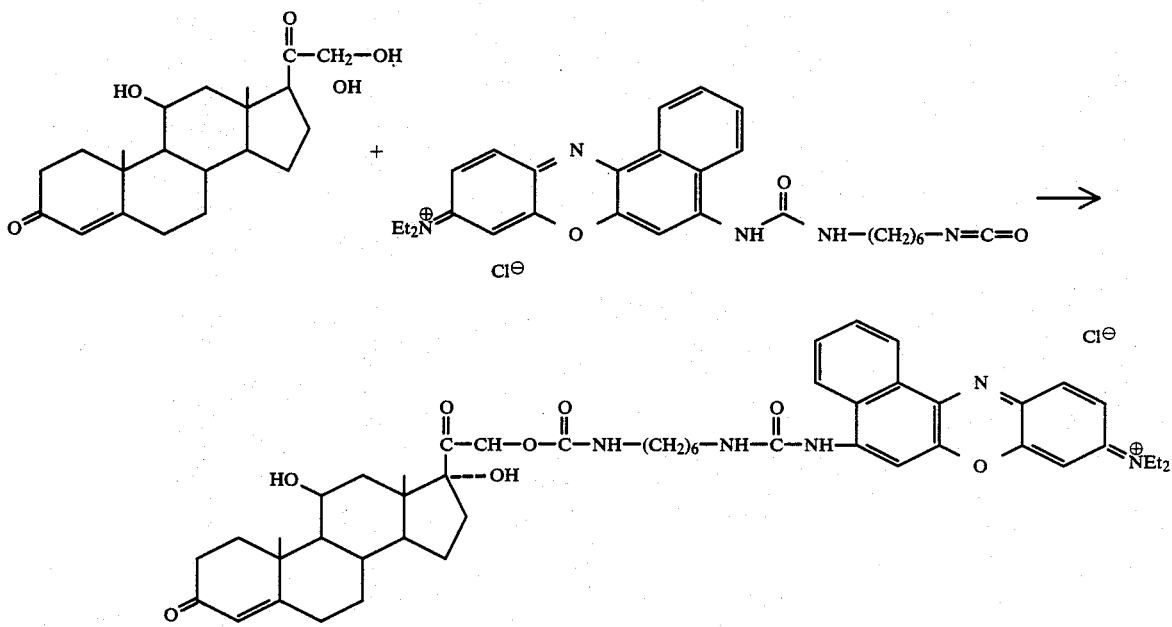

Thus, in accordance with the present invention adducts of urea derivatives of oxazine and thiazine chromophors and organic substrates can be illustrated by the following formulas:

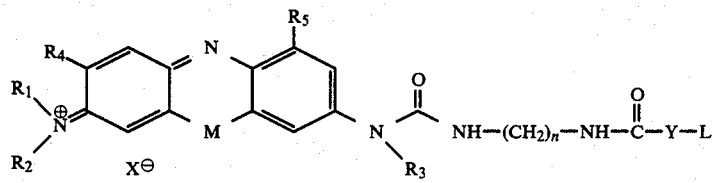

wherein n, M, $R_1$, $R_2$, $R_3$, $R_4$, $R_5$ and $X^\ominus$ are the same as defined in claim 1; Y is O, primary or secondary amine group, or S; L is an organic substrate containing a functional group having an active hydrogen selected from the group consisting of hydroxyl, amino, sulfhydryl, and carboxylic.

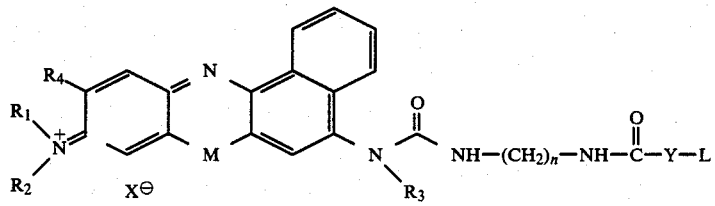

wherein n, M, $R_1$, $R_2$, $R_3$, $R_4$ and $X^\ominus$ Y and L are the same as defined

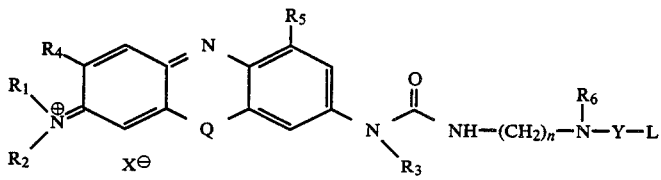

wherein n, M, $R_1$, $R_2$, $R_3$, $R_4$, $R_5$, and $X^\ominus$ are the same as defined in claim 1. $R_6$ is hydrogen, alkyl or aryl; Y is

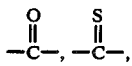

or $CH_2$; and when Y is

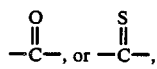

L is an organic substrate containing an active carboxylic, thiocarboxylic or dithiocarboxylic group and when Y is $CH_2$, L is an organic substrate containing an active halogen group.

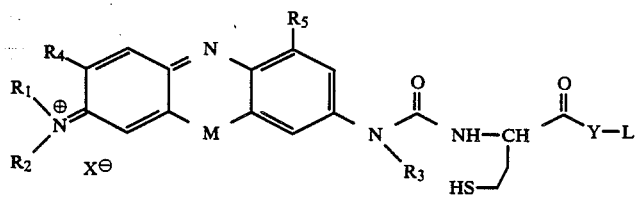

wherein n, M, $R_1$, $R_2$, $R_3$, $R_4$, $R_5$ and $X^\ominus$ are as defined in claim 1; Y is NH or NR', wherein R' is alkyl or aryl; and L is an organic substrate containing a functional group having an active hydrogen selected from the group consisting of primary or secondary amino groups.

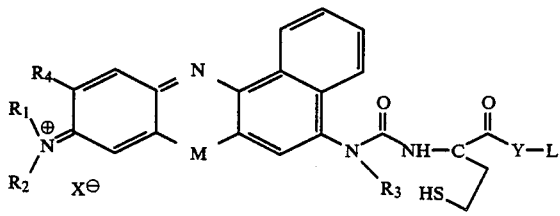

wherein M, $R_1$, $R_2$, $R_3$, $R_4$, $X^\ominus$, Y and L are as defined above. The isocyanato-alkyl-oxanine chromophors can be bound to organic substrates to form adducts by utilizing known process conditions. It is suitable, for example, to prepare the adduct by reaction in a solvent, if desired, at temperatures ranging from ambient to about 150° C. Representative examples of useful solvents which are inert to the isocyanato radicals include pyridine, tetrahydrofuran, dimethylformamide, triethylamine, ethers, methylene chloride and the like with pyridine being preferred. Also, if desired, any of the several types of catalysts known to be useful in forming urethanes, ureas, thioureas and amides can be employed. Useful catalysts include tertiary amines, salts or organic acids with a variety of metals such as alkali metals and the like. The conditions selected should be such as to insure that the structure of the compound or substrate of interest will not be degraded or otherwise adversely affected. For this reason, it is preferred to utilize as mild conditions as possible.

When the Z moiety is thiolactone as in butyrothiolactone-cresyl violet-urea, the resulting urea was well-suited to coupling with organic substrates having an active primary or secondary amine group. Typical organic substrates are proteins such as antibodies, enzymes, and drugs with active amine groups, receptive to an amide linkage. The following reaction of the thiolactone cresyl violet urea is illustrated:

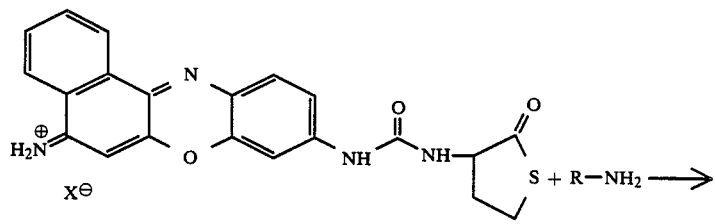

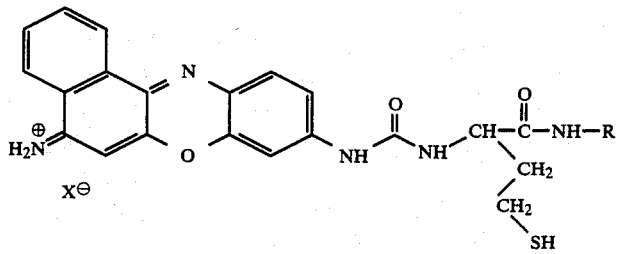

This coupling was carried out in a variety of solvents depending on the nature of the amine-substrate. The coupling of proteins was carried out in a variety of buffers, such as carbonates or phosphates. The pH of the reaction ranged from 1–12, but pH of 8 to 10 was preferred. The reaction time and temperature was appropriately selected depending on the stability and nature of the protein. The preferred reaction time was 1 to 24 hours and the preferred temperature was 4° C. to ambient. Since proteins may have more than one amino group, it is possible that more than one of the oxazine chromophors can be coupled. The coupling of one to five thiolactone-oxazine chromophors is preferred. The ratio of the chromophor to protein coupled can be controlled by the amount of the chromophor-thiolactone used. Other solvents such as, for example, pyridine formamides, amides, alcohols, ethers and chlorinated hydrocarbons inert to the reaction partners can be used where the nature of the organic substrate allows.

When the Z moiety is isothiocyanate, coupling occurs readily with an organic substrate containing a functional amine group having an active hydrogen which is receptive to thiourea linkage. The following reaction illustrates such a coupling.

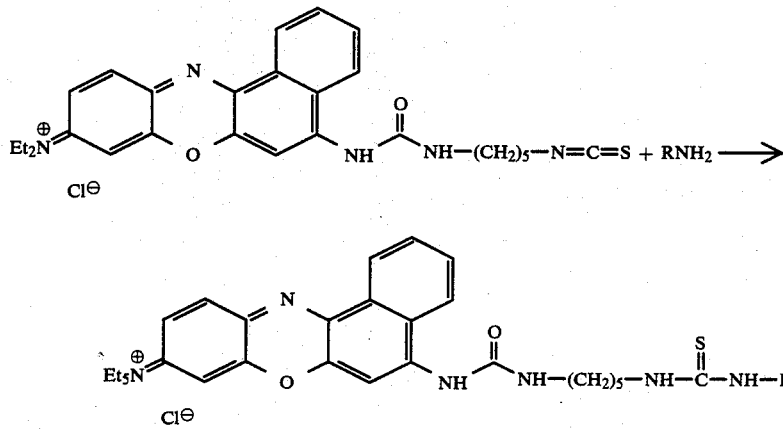

The conditions for the thiourea coupling are similar to the conditions used for the coupling of thiolactone-oxazine-urea.

As previously set forth, a urea derivatization of the oxazine chromphor which lead to functionalization of the chromophors, serving in further couplings, does not effectively change their physical properties (e.g., excitation, emission). Adducts of oxazine-urea derivatives with organic substrates of interest are intended for use in many of the several known techniques involving fluorescent tagging or fluorescent competitive binding to detect and measure a compound or substrate of interest. The particular adducts used will be dependent upon the type of tagging required by the technique of choice, and the technique selected will be determined by the results as required. The ureado-oxazine adducts are particularly advantageous since they exhibit little deleterious effects on the biological compounds, emit at wavelengths which are above 600 nanometers and show little overlap between excitation and emission.

Specific examples of compounds represented by formula I and II are

Brilliant cresyl blue

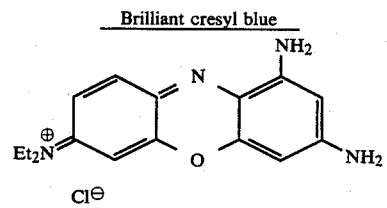

Nile blue A

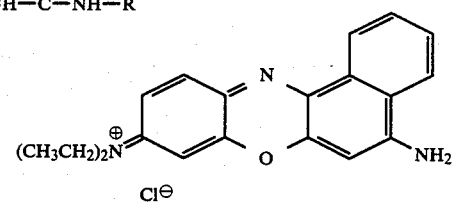

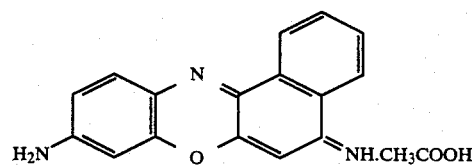

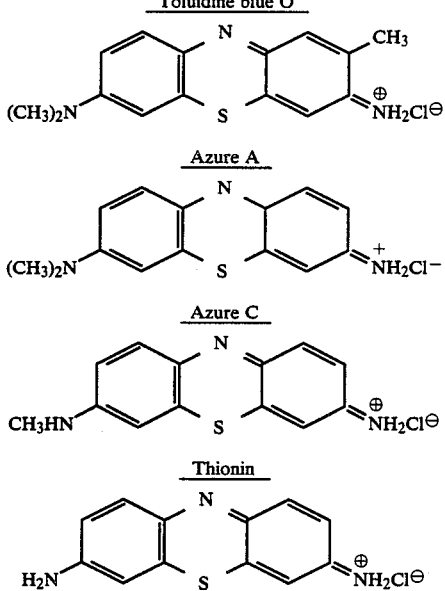

The following examples are illustrative but not in limitation of the present invention.

EXAMPLE 1

Isothiocyanato pentyl Nile blue A Urea

A mixture of 0.400 grams (1.1×10⁻³ mol) of Nile blue A and 0.3 milliliters (excess) of 1-isocyanato-5-isothiocyanato pentane was dissolved in 5.0 milliliters of dry pyridine and allowed to stir at ambient temperature for about 48 hours. The pyridine was then removed in vacuo at ambient temperature and the crude reaction mixture was washed with ether to remove unreacted 1-isocyanato-5-isothiocyanato pentane. Obtained was 0.520 grams of dark blue Nile blue A-isothiocyanate. IR (nujol) analysis showed bands at 3340 (NH), 2200 and 2130 (N=C=S), 1720, 1615, 1570, 1480, 1460, 1350, 1250, 1170, and 1010 cm⁻¹.

EXAMPLE 2

Isocyanatohexyl-Nile blue A Urea

A mixture of 450 mg of Nile blue A and 0.70 milliliters of 1,6-diisocyanato hexane was dissolved in 10 milliliters of dry pyridine and allowed to stir at ambient temperature for 6 days. The pyridine was then removed in vacuo at ambient temperature and the crude reaction mixture was washed with dry ether to remove unreacted diisocyanato hexane. 0.550 grams of isocyanatohexyl-Nile blue A-urea were obtained.

Since the isocyanato moiety was susceptible to hydrolysis, the product was used in its crude from. IR (pyridine) analysis showed bands of 3340 (NH), 2270 (N=C=O), 1700 cm⁻¹ (urea C=O).

EXAMPLE 3

N-(2-Thiolactone)-cresyl violet Urea

A mixture of 0.321 grams (1.0×10⁻³ mol) of cresyl violet acetate and 0.2 milliliter of 2-isocyanato butyrothio lactone were dissolved in 3 milliliter of dry methylene chloride and allowed to stir at ambient temperature for about 72 hours. The methylene chloride was then removed in vacuo and the product was washed with ether to remove unreacted isocyanate. 0.400 grams was obtained of blue solid product. This product characterized by infrared spectroscopy showed bands of 1720 and 1690 cm⁻¹ (thiolactone), 1640 cm⁻¹ (urea).

EXAMPLE 4

Isothiocyanato pentyl-toluidine blue O-urea

A mixture of 0.600 grams of toluidine blue and 0.3 milliliters (excess) of 1-isocyanato-5-isothiocyanato pentane was dissolved in 10 milliliter of dry pyridine and allowed to stir at ambient temperature for 6 days. The solvent was then removed in vacuo and the crude reaction mixture was washed with ether to remove unreacted isocyanate. 0.5 grams of drak blue product was obtained. IR (nujol) analysis showed bands at 3330 (NH), 2200-2130 (N=C=S), 1660 (urea), and 1610 cm⁻¹ (aromatic).

EXAMPLE 5

Isothiocyanato pentyl-brilliant cresyl blue-urea

A mixture of 0.332 grams (1×10⁻³ mol) of brilliant cresyl blue and 0.3 milliliter of 1-isocyanato-5-isothiocyanato pentane was dissolved in 5 milliliter of dry pyridine and allowed to stir at ambient temperature for 3 days. The solvent was removed in vacuo and the residue was washed with ether to remove unreacted 1-isocyanato-5-isothiocyanato pentane. 0.350 grams of product was obtained. IR (smear) analysis showed bands at 3.0μ (NH), 5.55–5.75 (N=C=S), 5.90, 6.08, 6.23 and 6.33μ.

Although the invention has been illustrated by the preceding examples, it is not to be construed as being limited to the materials employed therein, but rather, the invention is directed to the generic area as hereinbefore disclosed. Various modifications can be made without departing from the spirit or scope thereof.

What is claimed :

1. Urea derivatives of oxazine and thiazine chromophors selected from the group consisting of:

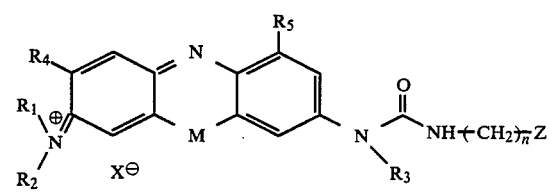

and

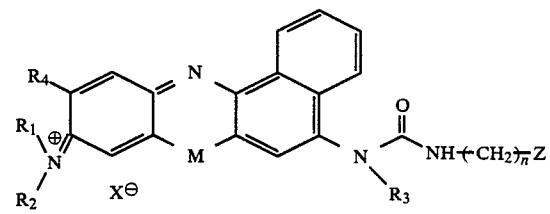

wherein n is 0 to 20; M is oxygen or sulfur; $R_1$ is hydrogen or alkyl group from 1 to 10 carbon atoms; $R_2$ is hydrogen or alkyl group from 1 to 10 carbon atoms; $R_3$ is hydrogen or alkyl group from 1 to 10 carbon atoms; $R_4$ is hydrogen, alkyl group from 1 to 10 carbon atoms, halogen or amino group; $R_5$ is hydrogen, alkyl group from 1 to 10 carbon atoms, halogen or amino group; $X^{\ominus}$ is an organic or an inorganic anion and Z is N=C=O, $N\!=\!C\!=\!S$, carboxylic, or amino, and when $n\!=\!0$, Z may be

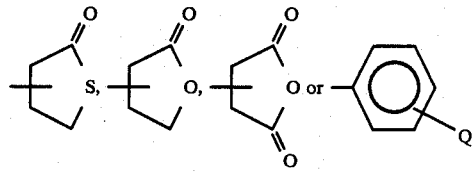

wherein Q is isocyanato or isothiocyanato.

2. Urea derivatives of oxazine and thiazine chromophors having the structural formula

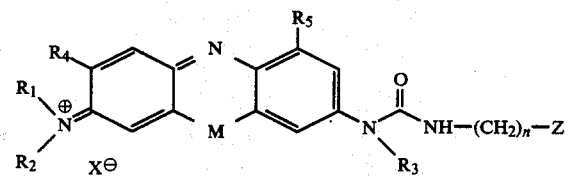

wherein n is 0 to 20; M is oxygen or sulfur; $R_1$ is hydrogen or alkyl group from 1 to 10 carbon atoms; $R_2$ is hydrogen or alkyl group from 1 to 10 carbon atoms; $R_3$ is hydrogen or alkyl group from 1 to 10 carbon atoms; $R_4$ is hydrogen, alkyl group from 1 to 10 carbon atoms, halogen or amino group; $R_5$ is hydrogen, alkyl group from 1 to 10 carbon atoms, halogen or amino group; $X^\ominus$ is an anion consisting of an organic specie $CH_3COO^\ominus$, $CH_3CH_2COO^\ominus$, or $CF_3COO^\ominus$, or an inorganic specie $Cl^\ominus$, $Br^\ominus$, $I^\ominus$, $ClO_4^\ominus$ or $SO_4^{-2}$, Z is $N\!=\!C\!=\!O$, $N\!=\!C\!=\!S$, carboxylic, or amino, and when $n\!=\!0$, Z may be

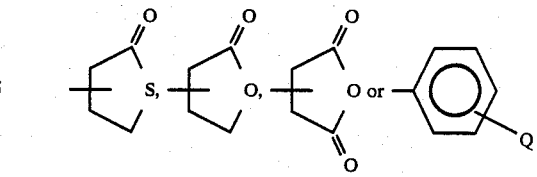

wherein Q is isocyanato or isothiocyanato.

3. Urea derivatives of oxazine and thiazine chormophors having the structural formula

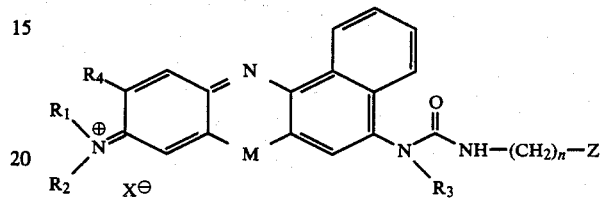

wherein n is 0 to 20; M is oxygen or sulfur; $R_1$ is hydrogen or alkyl group from 1 to 10 carbon atoms; $R_2$ is hydrogen or alkyl group from 1 to 10 carbon atoms; $R_3$ is hydrogen or alkyl group from 1 to 10 carbon atoms; $R_4$ is hydrogen, alkyl group from 1 to 10 carbon atoms, halogen or amino group; Z is $N\!=\!C\!=\!O$, $N\!=\!C\!=\!S$, carboxylic, or amino and when $n\!=\!0$, Z may be

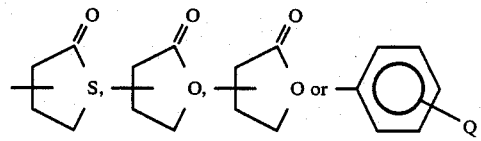

wherein Q is isocyanato or isothiocyanato, $X^\ominus$ is an anion consisting of an organic specie $CH_3COO^\ominus$, $CH_3CH_2COO^\ominus$, $CF_3COO^\ominus$ or an inorganic specie $Cl^\ominus$, $Br^\ominus$, $I^\ominus$, $ClO_4^\ominus$, $SO_4^{-2}$.

4. The urea derivative of claim 3 which is isothiocyanato pentyl Nile Blue A urea.

5. The urea derivative of claim 3 which is isocyanato-hexyl Nile Blue A urea.

6. The urea derivative of claim 3 which is N-(2-thiolactone)-cresyl violet urea.

7. The urea derivative of claim 2 which is isothiocyanato pentyl toluidine blue O urea.

8. The urea derivative of claim 2 which is isothiocyanato pentyl Brilliant cresyl blue urea.

* * * * *